United States Patent
Werden

(10) Patent No.: US 10,213,132 B2
(45) Date of Patent: *Feb. 26, 2019

(54) METHOD TO EVALUATE PATIENTS FOR THORACIC OUTLET SYNDROME

(71) Applicant: VANGUARD SPECIALTY IMAGING, INC., San Francisco, CA (US)

(72) Inventor: Scott A. Werden, San Francisco, CA (US)

(73) Assignee: Vanguard Specialty Imaging, Inc., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/270,890

(22) Filed: Sep. 20, 2016

(65) Prior Publication Data

US 2017/0071498 A1    Mar. 16, 2017

Related U.S. Application Data

(63) Continuation of application No. 14/629,310, filed on Feb. 23, 2015, now Pat. No. 9,474,463, which is a continuation of application No. 11/595,741, filed on Nov. 9, 2006, now Pat. No. 8,965,481.

(60) Provisional application No. 60/840,887, filed on Aug. 28, 2006.

(51) Int. Cl.
| | |
|---|---|
| *A61B 5/05* | (2006.01) |
| *A61B 5/055* | (2006.01) |
| *A61B 5/00* | (2006.01) |
| *A61B 5/02* | (2006.01) |

(52) U.S. Cl.
CPC .............. *A61B 5/055* (2013.01); *A61B 5/004* (2013.01); *A61B 5/02007* (2013.01); *A61B 5/7282* (2013.01); *A61B 2576/00* (2013.01)

(58) Field of Classification Search
CPC . A61B 2576/00; A61B 5/004; A61B 5/02007; A61B 5/055; A61B 5/7282
See application file for complete search history.

(56) References Cited

U.S. PATENT DOCUMENTS

| | | |
|---|---|---|
| 7,308,364 B2 | 12/2007 | Shaughnessy et al. |
| 8,965,481 B1 | 2/2015 | Werden |
| 9,474,463 B2 | 10/2016 | Werden |
| 2006/0167492 A1 | 7/2006 | Prince |
| 2007/0015995 A1 | 1/2007 | Lang et al. |

OTHER PUBLICATIONS

Pedrosa et al., "Effort-induced thrombosis: diagnosis with three-dimensional MR venography", Emergency Radiology, 2002, pp. 326-328.
Meaney et al., "MR Venography of the central veins: Comparison of Direct contrast-enhanced 2D MR fluoroscopic venography with 3D MRV", Proc. Intl. Soc. Mag. Reson. Med. 9 (2001), pp. 1945.
Grant, et al. "The Utility of Magnetic Resonance Imaging in Evaluating Peripheral Nerve Disorders", Muscle & Nerve, Mar. 2002.
Collins et al. "Scheuermann's Disease as a Model Displaying the Mechanism of Venous Obstruction in Thoracic Outlet Syndrome and Migraine Patients: MRI and MRA", 2003, Journal of the National medical Assoc. vol. 95, No. 4 298-306.
Collins et al., "Compromising Abnormalities of the Brachial Plexus as Displayed by Magnetic Resonance Imaging", 1995, Clinical Anatomy, 1-16.
Hagspeil et al., "Diagnosis of Vascular Compression at the Thoracic Outlet using Gladolinium-Enhanced High-Resolution Ultrafast MR Angiography in Abduction and Adduction", 2000, Cardiovascular and Interventional Radiology, 152-154.
Pedrosa et al., "Efforts-induced thrombosis: diagnosis with three-dimensional MR venography", Emergency Radiology, 2002, pp. 326-328.
Dymarkowski et al., "Three Dimensional MR Angiography in the Evaluation of Thoracic Outlet Syndrome", American Roentgen Ray Society, 1999, pp. 1005-1008.
Takahashi et al., "Is Half-Dose Contrast-Enhanced Three-Dimensional MR Angiography Sufficient for the Abdominal Aorta and Pelvis?", Journal of Magnetic Resonance Imaging, 2004, pp. 194-201.
Meaney et al., "MR Venography of the central veins Comparision of Direct contrast-enhanced 2D MR fluoroscopic venography with 3D MRV", Proc. Intl. Soc. Mag. Reson. Med. 9 (2001), pp. 1945.
Arlart et al., 12.4.8 Inflow Artifacts:, Magnetic Resonance Angiography—$2^{nd}$ Revised Edition, 2002, pp. 178-179, Springer-Verlag Berlin Heidelberg, Germany.
Lee, "Pseudostenosis", Cardiovascular MRI: Physical Principles to Practical Protocols, 2006, Lippincott Williams & Wilkins, Philadelphia, Pennsylvania.
Schneider et al., Figure 4, Magnetic Resonance Angiography—Techniques, Indications and Practical Applications, 2005, Springer-Verlag Italia, Italy.
Stepansky et al., "Dynamic MR Angiography of Upper Extremity Vascular Disease: Pictorial Review", RSNA Annual; meeting, 2006.
Grant et al., "The Utility of Magnetic Resonance Imaging in Evaluating Peripheral Nerve Disorders", Muscle Nerve 24: 314-331, 2002.

*Primary Examiner* — Christopher Cook
(74) *Attorney, Agent, or Firm* — Knobbe, Martens, Olson & Bear, LLP

(57) ABSTRACT

Methods to obtain three-dimensional models and images for diagnosis of Thoracic Outlet Syndrome are described.

9 Claims, No Drawings

METHOD TO EVALUATE PATIENTS FOR THORACIC OUTLET SYNDROME

CROSS-REFERENCE TO RELATED APPLICATIONS

This application is a continuation of U.S. patent application Ser. No. 14/629,310, titled METHOD TO EVALUATE PATIENTS FOR THORACIC OUTLET SYNDROME, filed Feb. 23, 2015, which is a continuation of U.S. patent application Ser. No. 11/595,741, titled METHOD TO EVALUATE PATIENTS FOR THORACIC OUTLET SYNDROME, filed Nov. 9, 2006, which claims benefit of U.S. Provisional Application No. 60/840,887, titled METHOD TO EVALUATE PATIENTS FOR THORACIC OUTLET SYNDROME, filed Aug. 28, 2006. Each of the foregoing applications is hereby incorporated by reference herein in its entirety.

TECHNICAL FIELD

The invention relates to methods of evaluating and diagnosing Thoracic Outlet Syndrome (TOS) using magnetic resonance imaging and magnetic resonance angiography.

BACKGROUND ART

The brachial plexus is a large cluster of nerves that passes from the spinal cord through the neck and the upper chest to the shoulder and arm. To reach the arm, the brachial plexus must pass through at least three anatomic tunnels. The main blood supply to and from the arm is provided by the subclavian artery and the subclavian vein, respectively. These major blood vessels pass through the same anatomic tunnels as the brachial plexus. Thoracic Outlet Syndrome (TOS) is a complex of signs and symptoms that results from narrowing of these tunnels and compression of one or more of these vital structures. TOS can be divided into three primary types:

Neurogenic Thoracic Outlet Syndrome: Neurogenic TOS is a compressive and entrapment neuropathy in which one or more of these tunnels becomes narrow, creating mechanical compression on the brachial plexus and/or altering its blood supply. This compression and altered blood flow result in pain, abnormal sensation, weakness, and eventual loss of muscle function in the affected areas.

Arterial Thoracic Outlet Syndrome: Arterial TOS results from mechanical compression of the subclavian or axillary artery, which causes arterial stenosis, post-stenotic aneurysm formation, and intramural thrombus formation. These changes result in decreased blood flow to the arm and/or embolism of thrombus to distal vessels, with pain, weakness, coldness and loss of pulse in the affected arm.

Venous Thoracic Outlet Syndrome: Venous TOS results from mechanical compression of the subclavian or axillary vein, which causes occlusive or non-occlusive thrombosis of the vein, damage to the lining of the vein, and eventual stricture formation that persists despite resolution of the extrinsic mechanical compression. These changes result in swelling, cyanosis, pain and altered function of the affected arm.

The causative mechanisms for all three types of primary TOS are nearly identical, and compression of one vital structure is often accompanied by compression of the other vital structures in varying degrees. Therefore, each primary type of TOS described above frequently includes a component of one or both of the other two types of TOS.

Thoracic Outlet Syndrome occurs when two conditions are met:

The patient has anatomic predispositions or anomalies. These can include abnormal muscles or fibrous bands, exaggeration or distortion of the usual shapes of the chest and shoulder girdle bony structures, anomalous courses of the nerves that make up the brachial plexus, or anomalous arteries or veins that pass through the thoracic outlet.

The patient has a superimposed traumatic event or repetitive overuse syndrome that:
Alters the soft tissues or bony structures that make up the anatomic tunnels, or
That causes direct injury to the brachial plexus, arteries, veins or soft tissues and bony structures that make up the anatomic tunnels, or
That alters the posture and position of the neck and shoulder girdle, leading to narrowing of the anatomic tunnels through which the brachial plexus, arteries and veins pass.

Neurogenic TOS is a compressive and entrapment neuropathy that has been clinically recognized for over one hundred years. Physicians frequently find these patients' cases complex and challenging. Patients often have a slowly-evolving course, experiencing symptoms intermittently early in the course of the disease and often only being symptomatic with the arms and neck in certain positions. As the disease progresses, the patients experience symptoms continuously, regardless of the position of their arms and neck. Patients often experience sensory changes early in the course of the disease, followed by vague muscle aching as the disease progresses. Eventually, patients experience muscle weakness, which in the late stages becomes evident as muscle atrophy and wasting, if the correct diagnosis is not made and definitive treatment is not undertaken. Unfortunately, when the disease progresses to this extent, muscle weakness and atrophy are unlikely to improve, even with definitive treatment.

Arterial TOS is frequently associated with an anomalous extra rib in the lower cervical spine, and was the first clinical form of TOS to be recognized, beginning with a case described in England in 1821, followed by a surgically proven case in 1861. It often has a dramatic clinical presentation due to either decreased blood flow to the affected arm or to the sudden development of blood clots embolizing to the distal vessels of the arm, causing gangrene. In this setting, the diagnosis is readily made. However, early diagnosis is critical to prevent the occurrence of these potentially serious complications.

Venous TOS frequently occurs in patients with an occupation requiring repetitive and/or strenuous use of their upper extremities, and is known by several other names, including effort thrombosis and Paget-Schroetter syndrome. It often has a dramatic clinical presentation due to swelling of the affected arm, decreased blood flow or loss of function. In addition, these patients are at risk of pulmonary embolism and pulmonary hypertension, either of which may be fatal. In this setting, the diagnosis is readily made. However, early diagnosis is critical to prevent the occurrence of potentially serious thromboembolic events, and to prevent permanent damage to the compressed vein, which predisposes the patient to repeated episodes of thrombosis formation and symptoms even after the mechanical compression of the vein has been treated.

Clinical, electrophysiologic and imaging tests have been developed over the past century, but none have been widely accepted as a gold standard for the diagnosis of TOS. Clinical tests utilize various positions of the patient's neck and arms while the pulse is palpated at the wrist. These tests have been shown to have a high number of false positive and false negative results. Electrophysiological tests are used to rule out the presence of other compressive and entrapment neuropathies of the upper extremity, but cannot confirm or rule out the diagnosis of TOS. Imaging tests have been used to evaluate the anatomy and pathology in patients with TOS. These tests have changed as the technology has evolved to allow more refined evaluation of anatomy and pathology in patients with TOS.

Since the 1960's, contrast angiography or venography has been performed to evaluate the arteries or veins of the arms, respectively, with the patient's arms placed in various provocative positions. This method duplicates the clinical tests in which the patient's pulse is palpated as their arms are moved into symptomatic positions. Angiography and venography are limited to evaluation of the compressed arteries and veins, but do not evaluate the abnormal anatomic tunnels that are causing this compression. Since the 1980's, CT scanning has been performed to evaluate the bony structures that border the thoracic outlet, or the arteries and veins of the arms, with the patient's arms placed in various provocative positions. CT scanning can also be performed with the patient's arms by their sides, allowing evaluation of the changes in the bony anatomic tunnels that occur with arm motion, and the resulting effects on the accompanying arteries or veins. CT scanning is limited in its evaluation of soft tissues, with inadequate differentiation of muscles and nerves in the thoracic outlet. Since the early 1990s, MRI scanning has been performed for the evaluation of soft tissue structures in the thoracic outlet, including the nerves of the brachial plexus, the arteries and veins of the arm, or the muscles that border the anatomic tunnels through which these vital structures pass to reach the arm. Like CT scanning, MRI scanning can be performed with the patient's arms placed in various provocative positions.

Each of these imaging tests has focused on one component of TOS, evaluating the bony structures, soft tissues, arteries, veins, or nerves. To date, there has been no single process that evaluates comprehensively the nerves, arteries and veins that pass through the thoracic outlet, the muscles and bony structures that form the anatomic tunnels of the thoracic outlet, the changes in the thoracic outlet that occur on arm movement, and the resulting effects of these changes on the brachial plexus, arteries and veins as they pass through these tunnels. The invention technique accomplishes these goals.

DISCLOSURE OF THE INVENTION

The invention provides a comprehensive process that permits accurate evaluation of patients for the presence or absence of Thoracic Outlet Syndrome (TOS). The invention employs magnetic resonance imaging techniques, magnetic resonance angiography and, optionally, magnetic resonance venography. Images are obtained as the basis for 3-dimensional models which are reviewed in addition to the original images by a radiologist according to a checklist of items with respect to each model and image.

Thus, in one aspect, the invention is directed to

A method to evaluate a human subject for the presence or absence of thoracic outlet syndrome (TOS) which method comprises:

a) obtaining a first set of magnetic resonance imaging (MRI) slices in each of three planes, in the absence of contrast agent, b) with the subject in a supine position with both arms in a neutral position by the side of the body, using a surface coil placed to cover the upper chest and neck, and the supraclavicular fossa region on the affected side(s), wherein a gradient echo T1, a spin-echo T1, or fast spin echo T2-weighted sequence comprises sagittal slices that cover the scalene triangle, costoclavicular space, and retropectoralis space on the affected side(s); and wherein a gradient echo T1, spin-echo T1, or fast spin echo T2-weighted sequence comprises axial slices that cover the mid and lower cervical spine and lower neck, and the brachial plexus, supraclavicular space, superior mediastinum and lung apex on the affected side(s); and wherein a Short Tau Inversion Recovery (STIR) sequence comprises coronal slices that cover the volume of the brachial plexus on the affected side(s);

b) obtaining a second set of MRI slices in one or more planes, with the subject in a supine position with both arms placed in abduction and external rotation, using a surface coil placed to cover the upper chest and neck, and the supraclavicular fossa region on the affected side(s), wherein the sequence that comprises the sagittal slices are obtained as in subparagraph a), in the absence of contrast agent, followed by an optional sequence that comprises the axial slices, obtained as in subparagraph a), in the absence of contrast agent, followed by intravenously administering a contrast agent, and obtaining a contrast-enhanced magnetic resonance angiogram (MRA) during the arterial enhancement phase following said administering which comprises coronal slices prescribed to cover the subclavian and axillary arteries on the affected side(s); after which, optionally obtaining a magnetic resonance venogram (MRV) performed during the arteriovenous equilibrium or venous enhancement phase following said administering which comprises coronal slices prescribed to cover the subclavian, axillary and brachiocephalic veins on the affected side(s);

c) composing the slices from the STIR sequence into a composite volume, and editing the composite volume to create a three-dimensional model of the brachial plexus on the affected side(s);

d) composing the slices from the MRA into a composite volume, and editing the composite volume to create a three-dimensional model of the arteries on the affected side(s); and e) composing the slices from the MRV, if performed, into a composite volume, and editing the composite volume to create a three-dimensional model of the veins on the affected side(s); and f) evaluating the first and second sets of MRI slices of a) and b) and the three-dimensional models of c) and d) and optionally e) according to a checklist, whereby the presence or absence of TOS in the subject is evaluated.

The evaluation data may also be stored on electronic media for future reference. Accordingly, in another aspect, the invention is directed to an electronic recording medium comprising evaluation data obtained according to the checklist described herein.

MODES FOR CARRYING OUT THE INVENTION

In general, the method of the invention involves obtaining a series of images, manipulating these images, and drawing conclusions from them according to a checklist of locations and evaluations. The radiologist will typically view and evaluate between 700 and 1,000 images displayed on a work station, for a patient who has both sides examined. A detailed description of the images to be obtained is as follows. While gadolinium is used as the contrast agent below, alternative similarly responding contrast agents, including but not limited to para-CEST agents may be used.

The patient is placed in supine position in the MRI scanner, with both arms in neutral position, by the side of the body. A neurovascular coil or similar coil that covers the upper chest, neck and supraclavicular fossa region on each side is used. The following sequences are then performed:

3D localizer sequence, using gradient recalled technique.
  Coronal STIR (Short Tau Inversion Recovery) sequence, prescribed to cover the volume of the brachial plexus on the affected side(s).
  Sagittal gradient echo T1, spin-echo T1 or fast spin echo T2-weighted sequence, prescribed to cover the scalene triangle, costoclavicular space and retropectoralis space on the affected side(s).
  Axial gradient echo T1, spin-echo T1 or fast spin echo T2-weighted sequence, prescribed to cover the mid and lower cervical spine and lower neck, and the brachial plexus, supraclavicular space, superior mediastinum and lung apex on the affected side(s).

The patient is then removed from the scanner, placed back in the scanner with both arms in abduction and external rotation, and a coil is placed to cover the patient's upper chest, neck and supraclavicular fossa region on each side. An intravenous line is placed in the patient's antecubital or hand vein at this time, if one has not already been placed earlier. This intravenous line is connected to a standard MRI power injector. The injector is pre-loaded with one syringe of normal saline (optional), and one syringe containing gadolinium contrast material, or a mixture of gadolinium contrast material and normal saline. The following sequences are then performed:

3D localizer sequence, using gradient recalled technique.
  Sagittal gradient echo T1, spin echo T1 or fast spin echo T2-weighted sequence, prescribed to cover the scalene triangle, costoclavicular space and retropectoralis space on the affected side(s).
  Axial gradient echo T1, spin echo T1 or fast spin echo T2-weighted sequence, prescribed to cover the mid and lower cervical spine and lower neck, and the brachial plexus, supraclavicular space, superior mediastinum and lung apex on the affected side(s).
  Time of flight angiogram, oriented in the coronal plane, prescribed to cover the subclavian, axillary and brachial artery on the affected side(s), performed during the arterial enhancement phase following injection of gadolinium contrast material via the previously placed intravenous line.
  Time of flight venogram, oriented in the coronal plane, prescribed to cover the subclavian, axillary and brachial artery and vein on the affected side(s), performed during the venous or equilibrium enhancement phase following injection of gadolinium contrast material via the previously placed intravenous line (this sequence is optional).

After the above images have been produced, the following reconstructions and reformations are performed on selected images:

The images from the STIR sequence are assembled into a volume and edited to create a 3-dimensional model of the brachial plexus on the affected side(s). This model can be displayed in any plane.
  The images from the time of flight angiogram are assembled into a volume and edited to create a 3-dimensional model of the arteries on the affected side(s). This model can be displayed in any plane.
  The images from the optional time of flight venogram are assembled into a volume and edited to create a 3-dimensional model of the veins on the affected side(s). This model can be displayed in any plane.

In patients with prior surgery for decompression of the thoracic outlet, the following optional sequences can be performed:

Axial gradient echo or fast spin echo T1 weighted sequence, prescribed to cover the surgical bed on the affected side(s).
  Sagittal gradient echo or fast spin echo T1 weighted sequence, prescribed to cover the surgical bed on the affected side(s).

This process may be described in further detail as follows: The patient is placed in supine position in the MRI scanner, with both arms in neutral position, by the side of the body. A neurovascular coil or similar coil that covers the upper chest, neck and supraclavicular fossa region on each side is used. The following sequences are then performed:

1. 3D localizer sequence, using gradient recalled technique.
  2. Oblique coronal STIR (Short Tau Inversion Recovery) sequence, oriented parallel to the C4/5 through C7IT1 neural foramina as seen on sagittal images of the localizer sequence. Slices are 3 mm thick, with 0 mm interstice gap, and are prescribed from the neural foramina posteriorly to the level of the anterior scalene muscles anteriorly on the affected side(s).
  3. Sagittal gradient echo T1 spin-echo T1 or fast spin echo T2-weighted sequence, with slice thickness of 4 mm, interslice gap of 0 mm, prescribed from the coracoid process on the left to the coracoid process on the right.
  4. Axial gradient echo T1, spin-echo T1, or fast spin echo T2-weighted sequence, with slice thickness of 4 mm, interslice gap of 0 mm, prescribed from the middle of the C4 body superiorly to the mid-portion of the aortic arch caudally.

The patient is then removed from the scanner, placed back in the scanner with both arms in hyperabduction and external rotation (approximately 135 degrees of abduction), and a torso PA coil is placed under the patient's back and over the patient's neck and chest to cover the upper chest, neck and supraclavicular fossa region on each side. An intravenous line is placed in the patient's antecubital or hand vein at this point in the study. The intravenous line is connected to a standard MRI power injector. The injector is pre-loaded with one syringe of normal saline, and one syringe containing a mixture of 30 cc of gadolinium contrast material and 30 cc of normal saline. The following sequences are then performed:

5. 3D localizer sequence, using gradient recalled technique.
  6. Sagittal gradient echo T1 spin-echo T1 or fast spin echo T2-weighted sequence, with slice thickness of 4 mm, interslice gap of 0 mm, prescribed from the coracoid process on the left to the coracoid process on the right.

7. Optional axial gradient echo T1, spin-echo T1 or fast spin echo T2-weighted sequence, with slice thickness of 4 mm, interslice gap of 0 mm, prescribed from the middle of the C6 body superiorly to the mid-portion of the aortic arch caudally.
8. Sagittal phase contrast angiogram, prescribed to cover the carotid and vertebral arteries in the neck.
9. Gradient recalled "black blood" sequence for timing of contrast injection. 2 cc of the solution containing 50% gadolinium contrast material and 50% normal saline is injected into the pre-existing intravenous line, starting at the same time as the sequence is initiated, and 30 axial images are obtained at the level of the carotid bifurcation, as determined by the preceding phase contrast sequence, at the rate of one image per second. These images are then evaluated for signal intensity using the 'functool' function of a GE Medical Systems MRI scanner console (or similar function available on all commercial scanners). A region of interest is placed over the carotid artery on these axial images, and the signal intensity over time is plotted, starting at time=0 seconds. The time from injection to peak signal intensity is determined and noted.
10. Magnetic resonance angiogram, oriented in the coronal plane, prescribed to cover both carotid and vertebral arteries as determined by the preceding phase contrast sequence (sequence 8). This sequence serves as a 'mask' for the next sequence, to allow reduction of artifact and reduction of background noise.
11. Contrast-enhanced magnetic resonance angiogram, oriented in the coronal plane, prescribed to cover both carotid and vertebral arteries as determined by the preceding phase contrast sequence (sequence 8). This sequence is initiated after the injection of the remainder of the 50% gadolinium contrast/50% saline solution pre-loaded into the power injector, utilizing the delay calculated in sequence 9, plus one second. Thus, the injection is initiated, the calculated delay is observed, and the sequence is initiated immediately after the delay elapses. This sequence produces source images for the magnetic resonance anglogram.
12. If desired, contrast-enhanced magnetic resonance venogram, oriented in the coronal plane, prescribed to cover both carotid and vertebral arteries as determined by the preceding phase contrast sequence. This sequence is an exact duplicate of the immediately previous sequence, (sequence 11), and is initiated immediately following the completion thereof. This sequence produces images of the arteries and veins of the upper chest, neck and upper extremities, which are source images for any desired magnetic resonance venogram.
13. Single shot fast spin echo sequence, oriented in the coronal plane, 10 mm slice thickness, single slice. This sequence is used to determine the presence or absence of fluid or edema in the soft tissues of the upper chest wall and supraclavicular fossae.

In patients with prior surgery for decompression of the thoracic outlet, the following sequences are then performed:

14. Axial gradient echo or fast spin echo T1-weighted sequence, with chemical fat suppression, slice thickness of 4 mm, and interslice gap of 0 mm. The slices are prescribed from the middle of the C6 body superiorly to the mid-portion of the aortic arch caudally.
15. Sagittal gradient echo or fast spin echo T1-weighted sequence, with chemical fat suppression, slice thickness of 4 mm, and interslice gap of 0 mm. The slices are prescribed from the midline of the spinal canal to the coracoid process on the post-surgical side(s).

After the above images have been produced, the following reconstructions and reformations are performed on selected images:

16. Each image from the oblique coronal STIR sequence is reviewed for the presence of brachial plexus components on the affected side(s). All images that contain these brachial plexus components are loaded into the Interactive Vascular Imaging (IVI) software program on the GE Medical Systems MRI scanner console (or similar function available on all commercial scanners), and the surrounding tissues are electronically removed in all planes, using the 'Modify Model-ThresholdNOI' function, leaving only the brachial plexus components on the affected side(s). One 3-dimensional model is constructed for each brachial plexus, including all components of the brachial plexus from the level of the neural foramina medially through the level of the retropectoralis space laterally on the affected side(s). Each 3-dimensional model is then rotated in the horizontal and vertical planes, using the 'Display Modes-Set Batch/Movie Loop' function. Thus, two models of each brachial plexus are constructed and saved for review.
17. Each image in sequence 10 is digitally subtracted from the corresponding image in sequence 11, producing a new set of images which represent source images for the arteriogram. These images are loaded into the Interactive Vascular Imaging (IVI) software program on the GE Medical Systems MRI scanner console (or similar function available on all commercial scanners), and the common carotid arteries, subclavian arteries, axillary arteries and brachial arteries on each side are identified. One projection image is constructed for the entire arterial tree, using a Maximal Intensity Projection (MIP) technique. The surrounding soft tissues are then electronically removed in all planes, using the 'Modify Model-Threshold/VOI' function, leaving only the major arteries on the affected side(s). A separate 3-dimensional model is then created for each arterial tree, including the common carotid artery, subclavian artery, axillary artery and brachial artery on the affected side(s) The 3-dimensional model created on each side is then rotated in the vertical plane, using the 'Display Modes-Set Batch/Movie Loop' function.
18. Optionally, each image in sequence 10 is digitally subtracted from the corresponding image in sequence 12, producing a new set of images which represent source images for the venogram. These images are loaded into the Interactive Vascular Imaging (IVI) software program on the GE Medical Systems MRI scanner console (or similar function available on all commercial scanners), and the common carotid arteries, subclavian arteries, axillary arteries, brachial arteries, internal jugular veins, subclavian veins, axillary veins and brachial veins on each side are identified. One projection image is constructed for the entire arterial and venous tree, using a Maximal Intensity Projection (MIP) technique. The surrounding soft tissues are then electronically removed in all planes, using the 'Modify Model-Threshold/VOI' function, leaving only the major arteries and veins on the affected side (s). A separate 3-dimensional model is then created for each combined arterial and venous tree, including the common carotid artery, subclavian artery, axillary artery, brachial artery, internal jugular vein, subclavian vein, axillary vein and brachial vein intact on the affected side(s). The 3-dimensional model created on each side is then rotated in the vertical plane, using the 'Display Modes-Set Batch/Movie Loop' function.

The complete set of 700-1,000 images is reviewed by a radiologist on a workstation. The anatomic and pathologic points of interest to be reviewed and reported are listed below.

In each case, the skilled radiologist will understand that the inspection will reveal the presence or absence of certain features and be able to identify those features that are associated with TOS. In some instances, as in the evaluation of the scalene muscles and certain other muscles of the right and left thoracic outlet, there appears no formal radiology literature on the appearance of these images, but surgery literature is available describing anatomic and pathologic changes in the areas of concern, and the skilled radiologist will be able to interpret these images on the basis of experience and knowledge of this literature.

Cervical spine disease
  Degenerative disc disease
  Degenerative joint disease
  Central canal or neural foraminal stenosis
  Integrity of spinal cord
Neck soft tissues
  Lymphadenopathy
  Soft tissue mass or cyst in neck, superior mediastinum, lung apices or supraclavicular fossae
Brachial plexus and other neural structures
  Branching pattern, caliber and signal intensity of brachial plexus
  Nerve root avulsion or pseudomeningocoele
  Size and symmetry of stellate ganglia
Metrics of cervicothoracic junction
  Superior thoracic aperture: measured from the posterior border of the superior aspect of the manubrium to the anterior cortex of the vertebral column, in the horizontal plane, as seen on the midline sagittal image
    Measured in both arms neutral and hyperabduction-external rotation positions
  First rib angle: measured relative to the horizontal, as seen on the sagittal image demonstrating the longest segment of first rib
    Measured in both arms neutral and hyperabduction-external rotation positions
  C7 vertebral anatomy
    Bony tubercles of body
    Bony bars, extending to transverse processes and forming pseudo-transverse foramina
    Enlarged transverse processes
    Cervical ribs
Right thoracic outlet
  Scalene muscles
    Size
    Origins
    Insertions
    Interdigitating muscle bands
    Scalene minimus muscles
    Fibrous bands
    Levator costae muscles
    Slings
  Scalene triangle-arms neutral
    Apex
    Base
  Brachial plexus
    Course relative to scalene muscles, scalene triangle and anomalies of structures in "Right thoracic outlet, Scalene muscles" listed above.
  Other muscles
    Subclavius
      Size
      Subclavius posticus variant
    Pectoralis minor
    Axillary arch
  Anatomic tunnels-hyperabduction external rotation
    Scalene Triangle
    Costoclavicular interval
    Subclavius-Serratus space
    Retropectoralis space
Left thoracic outlet
  Scalene muscles
    Size
    Origins
    Insertions
    Interdigitating muscle bands
    Scalene minimus muscles
    Fibrous bands
    Levator costae muscles
    Slings
  Scalene triangle-arms neutral
    Apex
    Base
  Brachial plexus
    Course relative to scalene muscles, scalene triangle and anomalies of structures in "Right thoracic outlet, Scalene muscles" listed above.
  Other muscles
    Subclavius
      Size
      Subclavius posticus variant
    Pectoralis minor
    Axillary arch
Anatomic tunnels-hyperabduction external rotation
  Scalene Triangle
  Costoclavicular interval
  Subclavius-Serratus space
  Retropectoralis space
MR Angiogram
  Aortic arch branching pattern
  Great vessels and other major branches
    Common carotid arteries
    Vertebral arteries
    Internal mammary arteries
    Subclavian, axillary and brachial arteries as they pass through anatomic tunnels
    Dorsal scapular arteries and transverse arteries
  Evaluate vessels for
    Extrinsic compression
    Intrinsic stenosis, or vascular disease
    Post-stenotic dilatation
    Anomalous course or vessel
MR Venogram
  Neutral position
    Subclavian and axillary veins
    Left brachiocephalic vein
      Compression in superior mediastinum
    Internal and external jugular veins, and cephalic veins
  Hyperabduction external rotation
    Subclavian and axillary veins
    Left brachiocephalic vein
      Compression in superior mediastinum
    Internal and external jugular veins, and cephalic veins Evaluate vessels for
    Extrinsic compression
    Thrombus
    Slowing of flow
        Suggested by increased luminal signal intensity
        Change in caliber between neutral and hyperabduction external rotation
    Presence of gadolinium contrast in veins
Lymphatics
    Thoracic duct
    Supraclavicular lymphatics
    Edema of supraclavicular fossae or chest wall

What is claimed is:

1. A method of generating and outputting a plurality of three-dimensional models and a plurality of series of images to evaluate a human subject for a presence or absence of thoracic outlet syndrome (TOS) which method comprises:
    generating a first three-dimensional model of a brachial plexus on an affected side(s), the first three-dimensional model generated based at least in part on reconstruction and reformation of a first set of magnetic resonance imaging (MRI) slices obtained in each of three planes, in the absence of a contrast agent, with a subject in a supine position with both arms in a neutral position by a side of a body of the subject, wherein obtaining the first set of MRI slices is configured to comprise:
        obtaining a gradient echo T1, spin echo T1, or fast spin echo T2-weighted sequence that comprises sagittal slices that cover scalene triangle, costoclavicular space, and retropectoralis spaces on an affected side(s);
        obtaining another gradient echo T1, spin echo T1, or fast spin echo T2-weighted sequence that comprises axial slices that cover mid and lower cervical spinal portions, lower neck, the brachial plexus, supraclavicular space, superior mediastinum, and lung apex on the affected side(s); and
        obtaining a Short Tau Inversion Recovery (STIR) sequence that comprises slices that cover a volume of the brachial plexus on the affected side(s);
    outputting a first series of images including the first set of MRI slices, to be displayed on a workstation to determine, based at least in part on the first set of MRI slices, a presence or absence of stenosis and to determine the presence or absence of thoracic outlet syndrome (TOS);
    outputting the first three-dimensional model to the workstation to determine the presence or absence of thoracic outlet syndrome (TOS);
    obtaining a second set of MRI slices obtained in one or more planes, in the absence of the contrast agent, with the subject in a supine position with both arms placed in abduction and external rotation, by imaging upper chest and neck portions and a supraclavicular fossa region on the affected side(s), wherein the second set of MRI slices is configured to be obtained by the gradient echo T1, spin echo T1, or fast spin echo T2-weighted sequence that comprises sagittal slices that cover scalene triangle, costoclavicular space and retropectoralis space on the affected side(s);
    outputting a second series of images including the second set of MRI slices, to be displayed on the workstation to determine, based at least in part on the second set of MRI slices, the presence or absence of stenosis and to determine the presence or absence of thoracic outlet syndrome (TOS);
    generating a second three-dimensional model of arteries on the affected side(s), the second three-dimensional model generated based at least in part on reconstruction and reformation of a plurality of slices from a contrast-enhanced magnetic resonance angiogram (MRA), wherein the plurality of MRA slices images subclavian and axillary arteries on both sides of the subject, wherein the plurality of MRA slices are configured to be obtained by administering a diluted contrast agent comprising 50% gadolinium into a vein on a first side of the subject such that the contrast agent enters arteries on both sides of the subject and veins on both sides of the subject and obtaining a contrast-enhanced MRA, which images, in the subject, the contrast agent;
    outputting a third series of images including the plurality of MRA slices, to be displayed on the workstation to determine, based at least in part on the plurality of MRA slices, a presence or absence of stenosis, external compression, or aneurysm, if any, in each of the subclavian and the axillary arteries by assessing vascular contrast enhancement, on both sides of the subject and to determine the presence or absence of thoracic outlet syndrome (TOS);
    outputting the second three-dimensional model to the workstation to determine the presence or absence of thoracic outlet syndrome (TOS);
    generating a third three-dimensional model of veins on the affected side(s), the third three-dimensional model generated based at least in part on reconstruction and reformation of a plurality of slices from a magnetic resonance venogram (MRV), wherein the plurality of MRV slices images the subclavian, axillary, and brachiocephalic veins on both sides of the subject, wherein the plurality of MRV slices are configured to be obtained by administering the diluted contrast agent comprising 50% gadolinium into the vein on the first side of the subject such that the contrast agent enters arteries on both sides of the subject and veins on both sides of the subject and obtaining the MRV, which images, in the subject, the contrast agent;
    outputting a fourth series of images including the plurality of MRV slices, to be displayed on the workstation to determine, based at least in part on the plurality of MRV slices, the presence or absence of stenosis or external compression in each of the subclavian, axillary, and brachiocephalic veins on both sides of the subject by assessing vascular contrast enhancement, on both sides of the subject and to determine the presence or absence of thoracic outlet syndrome (TOS); and
    outputting the third three-dimensional model to the workstation to determine the presence or absence of thoracic outlet syndrome (TOS).

2. The method of claim 1, wherein the contrast agent further comprises 50% normal saline.

3. The method of claim 1, wherein the arteries comprise upper extremity arteries and wherein the veins comprise upper extremity veins.

4. The method of claim 1, wherein the obtaining the first set of MRI slices is further configured to comprise disposing a surface coil over the subject to cover the upper chest and neck and the supraclavicular fossa region on the affected side(s).

5. A method of generating and outputting a plurality of three-dimensional models and a plurality of series of images to evaluate a human subject for a presence or absence of thoracic outlet syndrome (TOS) which method comprises:

generating a first three-dimensional model of a brachial plexus on an affected side(s), the first three-dimensional model generated based at least in part on reconstruction and reformation of a first set of magnetic resonance imaging (MRI) slices obtained in each of three planes, in the absence of a contrast agent, with a subject in a supine position with both arms in a neutral position by a side of a body of the subject, wherein obtaining the first set of MRI slices is configured to comprise:
 obtaining a gradient echo, spin echo, or fast spin echo sequence that comprises sagittal slices that cover a thoracic outlet on an affected side(s);
 obtaining another gradient echo, spin echo, or fast spin echo sequence that comprises axial slices that cover mid and lower cervical spinal portions, lower neck, the brachial plexus, supraclavicular space, superior mediastinum and lung apex on the affected side(s); and
 obtaining a Short Tau Inversion Recovery (STIR) sequence that comprises slices that cover a volume of the brachial plexus on the affected side(s);
outputting a first series of images including the first set of MRI slices, to be displayed on a workstation to determine, based at least in part on the first set of MRI slices, a presence or absence Of stenosis and to determine the presence or absence of thoracic outlet syndrome (TOS);
outputting the first three-dimensional model to the workstation for evaluation to determine the presence or absence of thoracic outlet syndrome (TOS);
obtaining a second set of MRI slices obtained in one or more planes, in the absence of the contrast agent, with the subject in a supine position with both arms in abduction and external rotation, by imaging upper chest and neck portions and a supraclavicular fossa region on the affected side(s), wherein the second set of MRI slices is configured to be obtained by the gradient echo, spin echo, or fast spin echo sequence that comprises sagittal slices that cover the thoracic outlet on the affected side(s);
outputting a second series of images including the second set of MRI slices, to be displayed on the workstation to determine, based at least in part on the second set of MRI slices, the presence or absence of stenosis and to determine the presence or absence of thoracic outlet syndrome (TOS);
generating a second three-dimensional model of arteries on the affected side(s), the second three-dimensional model generated based at least in part on reconstruction and reformation of a plurality of slices from a contrast-enhanced magnetic resonance angiogram (MRA), wherein the plurality of MRA slices images subclavian and axillary arteries on both sides of the subject, wherein the plurality of MRA slices are configured to be obtained by administering a diluted contrast agent comprising 50% gadolinium into a vein on a first side of the subject such that the contrast agent enters arteries on both sides of the subject and veins on both sides of the subject and obtaining a contrast-enhanced MRA, which images, in the subject, the contrast agent; and
outputting a third series of images including the plurality of MRA slices, to be displayed on the workstation to determine, based at least in part on the plurality of MRA slices, a presence or absence of stenosis, external compression, or aneurysm, if any, in each of the subclavian and the axillary arteries by assessing vascular contrast enhancement, on both sides of the subject and to determine the presence or absence of thoracic outlet syndrome (TOS);
outputting the second three-dimensional model to the workstation to determine the presence or absence of thoracic outlet syndrome (TOS);
generating a third three-dimensional model of veins on the affected side(s), the third three-dimensional model generated based at least in part on reconstruction and reformation of a plurality of slices from a magnetic resonance venogram (MRV), wherein the plurality of MRV slices images the subclavian, axillary, and brachiocephalic veins on both sides of the subject, wherein the plurality of MRV slices are configured to be obtained by administering the diluted contrast agent comprising 50% gadolinium into the vein on the first side of the subject such that the contrast agent enters arteries on both sides of the subject and veins on both sides of the subject and obtaining the MRV, which images, in the subject, the contrast agent;
outputting a fourth series of images including the plurality of MRV slices, to be displayed on the workstation to determine, based at least in part on the plurality of MRV slices, the presence or absence of stenosis or external compression in each of the subclavian, axillary, and brachiocephalic veins on both sides of the subject by assessing vascular contrast enhancement, on both sides of the subject and to determine the presence or absence of thoracic outlet syndrome (TOS); and
outputting the third three-dimensional model to the workstation to determine the presence or absence of thoracic outlet syndrome (TOS).

6. The method of claim 5, wherein the contrast agent further comprises 50% normal saline.

7. The method of claim 5, wherein the arteries comprise upper extremity arteries and wherein the veins comprise upper extremity veins.

8. The method of claim 5, wherein the obtaining the first set of MRI slices is further configured to comprise disposing a surface coil over the subject to cover the upper chest and neck and the supraclavicular fossa region on the affected side(s).

9. The method of claim 5, wherein the thoracic outlet comprises a scalene triangle, a costoclavicular space, and a rectropectoralis space.

* * * * *